(12) United States Patent
Li et al.

(10) Patent No.: US 10,722,194 B2
(45) Date of Patent: Jul. 28, 2020

(54) X-RAY DETECTOR FOR MEDICAL DIAGNOSIS

(71) Applicant: GENERAL ELECTRIC COMPANY, Schenectay, NY (US)

(72) Inventors: Hui Li, Beijing (CN); Nicholas Ryan Konkle, Waukesha, WI (US); Tao Chen, Beijing (CN); Gaoling Liu, Beijing (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 268 days.

(21) Appl. No.: 15/524,970

(22) PCT Filed: Nov. 6, 2014

(86) PCT No.: PCT/CN2014/090487
§ 371 (c)(1),
(2) Date: Oct. 2, 2017

(87) PCT Pub. No.: WO2016/070385
PCT Pub. Date: May 12, 2016

(65) Prior Publication Data
US 2018/0028134 A1    Feb. 1, 2018

(51) Int. Cl.
*A61B 6/00*    (2006.01)
*G01T 1/20*    (2006.01)

(52) U.S. Cl.
CPC .............. *A61B 6/4233* (2013.01); *A61B 6/00* (2013.01); *G01T 1/2018* (2013.01)

(58) Field of Classification Search
CPC ........ A61B 6/4233; A61B 6/00; G01T 1/2018
(Continued)

(56) References Cited

U.S. PATENT DOCUMENTS 4,939,054 A * 7/1990 Hotomi .............. G03G 5/08221
430/58.1
6,310,358 B1 * 10/2001 Zur ...................... G01T 1/2018
250/338.4
(Continued)

FOREIGN PATENT DOCUMENTS

CN    1211413 A    3/1999
CN    103054592 A    4/2013
(Continued)

OTHER PUBLICATIONS

Extended European Search Report and Opinion issued in connection with corresponding EP Application No. 14905472.8 dated Jul. 2, 2018.
(Continued)

*Primary Examiner* — Taeho Jo
(74) *Attorney, Agent, or Firm* — Fletcher Yoder, P.C.

(57) ABSTRACT

The present invention provides a detector for medical diagnosis. The detector for diagnosis includes a photosensitive element, an X-beam stopping element, a supporting board, and a conductive liner. The photosensitive element is used for sensing an X-beam. The X-beam stopping element is used for stopping the X-beam from penetrating said photosensitive element. The supporting board is provided below the X-beam stopping element to be used for supporting said photosensitive element. The conductive liner is provided between said photosensitive element and said supporting board to fit with said photosensitive element.

7 Claims, 2 Drawing Sheets

(58) Field of Classification Search
USPC .................................................... 378/189
See application file for complete search history.

(56) References Cited

U.S. PATENT DOCUMENTS

| | | | | |
|---|---|---|---|---|
| 6,553,092 B1* | 4/2003 | Mattson | ............... | G01T 1/2018 250/370.11 |
| 7,709,803 B2* | 5/2010 | Adachi | ............... | G01T 1/244 250/370.09 |
| 10,007,007 B2* | 6/2018 | Cao | ............... | H01L 27/14609 |
| 2003/0100138 A1* | 5/2003 | Izumi | ............... | H01L 31/02161 438/68 |
| 2004/0016886 A1* | 1/2004 | Ringermacher | .. | H01L 27/14601 250/370.11 |
| 2006/0035168 A1* | 2/2006 | Goi | ............... | G03C 3/00 430/270.1 |
| 2006/0065846 A1* | 3/2006 | Ertel | ............... | G01T 1/2018 250/370.11 |
| 2007/0045553 A1* | 3/2007 | Adachi | ............... | G01T 1/244 250/370.09 |
| 2008/0078938 A1* | 4/2008 | Vafi | ............... | G01T 1/2018 250/370.09 |
| 2008/0116385 A1* | 5/2008 | Yuuya | ............... | H01L 27/14683 250/370.08 |
| 2009/0014659 A1* | 1/2009 | Hennessy | ............... | G01T 1/2018 250/370.09 |
| 2010/0230607 A1* | 9/2010 | Kitada | ............... | G01T 1/241 250/370.08 |
| 2011/0158387 A1* | 6/2011 | Narayanaswamy | ...... | G01T 1/20 378/62 |
| 2011/0315978 A1* | 12/2011 | Furui | ............... | H01L 27/14676 257/42 |
| 2012/0025089 A1* | 2/2012 | Takagi | ............... | H01L 31/115 250/370.09 |
| 2013/0083900 A1* | 4/2013 | Kobayashi | ............ | G03B 42/04 378/189 |
| 2013/0099126 A1* | 4/2013 | Iwata | ............... | G01T 1/2018 250/366 |
| 2013/0099130 A1* | 4/2013 | Nakahashi | ............... | A61B 6/00 250/394 |
| 2013/0220514 A1 | 8/2013 | Jagannathan et al. | | |
| 2014/0016886 A1 | 1/2014 | Li et al. | | |
| 2014/0346631 A1* | 11/2014 | Karim | ............... | H01L 31/18 257/435 |
| 2016/0111473 A1* | 4/2016 | Liu | ............... | H01L 51/0021 378/51 |

FOREIGN PATENT DOCUMENTS

| | | |
|---|---|---|
| CN | 203647367 U | 6/2014 |
| JP | 2006-025829 A | 2/2006 |
| JP | 2006025829 * | 2/2006 |
| JP | 2013-108974 A | 6/2013 |

OTHER PUBLICATIONS

Machine translation and Notification of Reasons for Refusal issued in connection with corresponding JP Application No. 2017-523350 dated Jul. 3, 2018.
International Search Report and Written Opinion for PCT/CN2014/090487, dated May 28, 2015, 12 pages.
English Translation of International Search Report for PCT/CN2014/090487, dated May 28, 2015, 2 pages.

* cited by examiner

X-RAY DETECTOR FOR MEDICAL DIAGNOSIS

CROSS-REFERENCE TO RELATED APPLICATIONS

This application is a US PCT National Phase filing under 35 U.S.C. 371 of co-pending International Application No. PCT/CN2014/090487, filed Nov. 6, 2014, which is incorporated herein by reference in its entirety.

BACKGROUND

As an image-diagnostics examining system, the X-beam diagnosis system has been widely used to examine the body and form image data in order to allow a doctor to perform diagnosis easily. As a very important unit in the X-beam diagnosis system, the X-beam detector affects the quality of the image diagnosed by the system directly.

Usually, during the X-beam diagnosis, the X-beam detector may sense an X-beam penetrating a diagnosed object by a photosensitive element (e.g., a glass panel) provided therein, and collect data on an X-beam signal sensed by the photosensitive element by a data collection module and thereafter transmits the data to a control board, so as to sequentially perform an imaging process on the collected data later.

In some existing X-beam detectors, a supporting board (or called as a back board or a cold board), an X-beam stopper provided on the supporting board, an aluminum board, a black ethylene film provided on the aluminum board, and a photosensitive element are provided. The photosensitive element is provided on the aluminum board and fits closely with the aluminum board, thereby removing static electricity from the photosensitive element by the aluminum board.

However, in the existing designs, since the panel is needed to fit closely with the aluminum board, the requirement for the precision of processing the aluminum board is very high, which increases the processing difficulty and the manufacturing cost. Moreover, such structure cannot very well solve the problem that the external vibration or shock results in the deformation and smash of the glass panel.

There have already been some other attempts to solve the above problem. For example, instead of providing the aluminum board, a conductive material is sprayed on the back face of the glass panel, thus removing static electricity from the photosensitive element. However, the sprayed material may pollute the environment, and a good control is needed for the spraying process, which increases the complexity of manufacturing the detector, thus resulting in an adverse effect on the manufacturing.

Therefore, there is a need to provide a novel X-image detector for diagnosis, which may ensure very well that while the detector has a relatively high and stable performance, the manufacturing difficulty and cost are decreased.

SUMMARY

At least one embodiment of the present disclosure provides a detector for medical diagnosis. The detector includes a photosensitive element, an X-beam stopping element, a supporting board, and a conductive liner. The photosensitive element is used for sensing an X-beam. The X-beam stopping element is used for stopping the X-beam penetrating said photosensitive element. The supporting board is provided below the X-beam stopping element to be used for supporting said photosensitive element. The conductive liner is provided between said photosensitive element and said supporting board to fit with said photosensitive element.

BRIEF DESCRIPTION OF THE DRAWINGS

The non-limiting embodiments disclosed herein can be understood better in light of the detailed description with reference to the accompanying drawings, in which.

DETAILED DESCRIPTION

Hereafter, a detailed description will be given for the non-limiting embodiments presented herein. It should be pointed out that in the detailed description of the embodiments, for simplicity and conciseness, it is impossible for the description to describe all the features of the practical embodiments in details. It should be understood that in the process of a practical implementation of any embodiment, just as in the process of an engineering project or a designing project, in order to achieve a specific goal of the developer and in order to satisfy some system-related or business-related constraints, a variety of decisions will usually be made, which will also be varied from one embodiment to another. In addition, it can also be understood that although the effort made in such developing process may be complex and time-consuming, some variations such as design, manufacture and production on the basis of the technical contents disclosed in the disclosure are just customary technical apparatus in the art for those of ordinary skilled in the art relating to the contents disclosed herein, which should not be regarded as insufficient disclosure of the embodiments described herein.

Unless defined otherwise, all the technical or scientific terms used in the claims and the description should have the same meanings as commonly understood by one of ordinary skilled in the art to which the present invention belongs. The terms "first", "second" and the like in the description and the claims of the present application do not mean any sequential order, number or importance, but are only used for distinguishing different components. The terms "a", "an" and the like do not denote a limitation of quantity, but denote the existence of at least one. The terms "comprises", "comprising", "includes", "including" and the like mean that the element or object in front of the "comprises", "comprising", "includes" and "including" encompasses the elements or objects and their equivalents illustrated following the "comprises", "comprising", "includes" and "including", but do not exclude other elements or objects. The term "coupled", "connected" or the like is not limited to being connected physically or mechanically, nor limited to being connected directly or indirectly.

Figure 1:
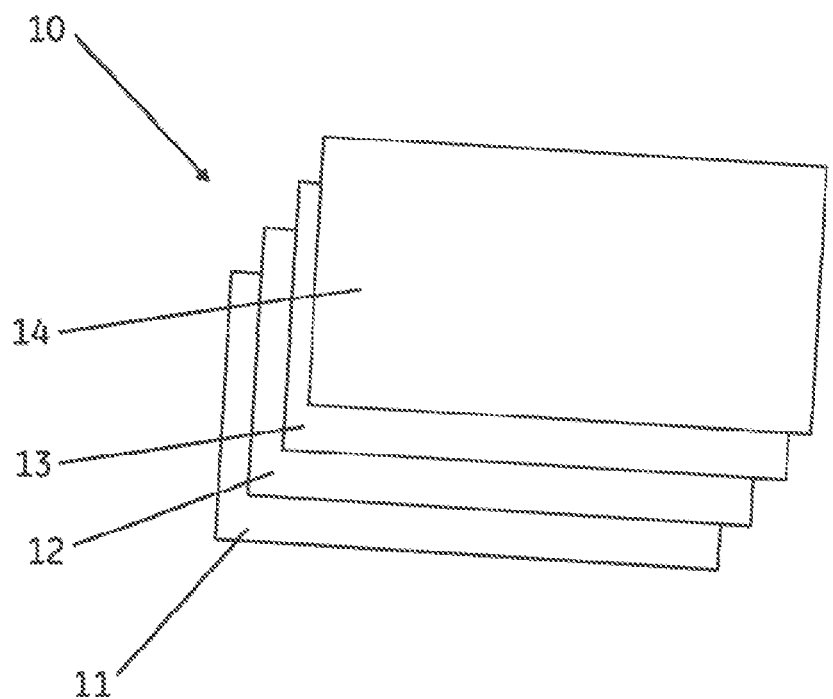
FIG. 1 is a decomposition schematic diagram of one embodiment of a detector.
Figure 2:
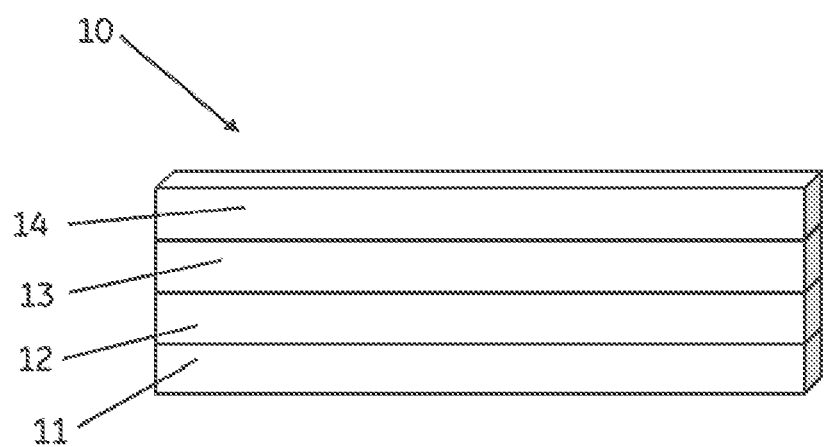
FIG. 2 is an assembly schematic diagram of one embodiment of the detector shown in FIG. 1.

FIG. 1 illustrates a decomposition schematic diagram of one embodiment of a detector 10 for medical diagnosis. FIG. 2 illustrates an assembly schematic diagram of one embodiment of the detector 10. In this non-limiting embodiment, the structure of the detector 10 is merely illustrative, and in different applications, the detector 10 may also include other structures or elements (not shown) to implement the detecting function of the detector.

As shown in FIG. 1 to FIG. 2, the detector 10 comprises a supporting board 11, an X-beam stopper 12, a conductive liner 13, and a photosensitive element 14. The supporting board 11 is provided below the detector 10 to support other elements or structures of the detector 10. In a non-limitative example, the supporting board 11 is made of metal material, and may also be called as a back board or used as a cold board.

The X-beam stopper 12 is provided at an upper surface (not labeled) of the supporting board 11, i.e., the supporting board 11 is provided below the X-beam stopper 12. In a non-limitative example, the X-beam stopper 12 usually includes plumbum material or tungsten material. During the detection made by the detector 10, the X-beam stopper 12 may be used to stop the X-beam penetrating the photosensitive element 14, avoiding the X-beam from further penetrating the back board 11 to enter the external environment to cause adverse results.

The conductive liner 13 is provided on the X-beam stopper 12. The photosensitive element 14 may be used to sense the X-beam penetrating the diagnosed object, and is provided on the conductive liner 13, such that the conductive liner 13 is located between the photosensitive element 14 and the X-beam stopper 12 or the back board 11. In at least one embodiment, the conductive liner 13 is a flexible liner, and the photosensitive element 14 may include a glass panel. In this way, the glass panel 14 may be more easily provided on the conductive liner 13 and fit with the conductive liner 13, such that the conductive liner 13 may play the role of grounding or removing the static electricity. Meanwhile, since the conductive liner 13 is elastic to some extent, it may buffer the external vibration or shock so as to protect the glass panel from being damaged. In some examples, the conductive liner 13 may be any suitable liner.

In at least one embodiment, the conductive liner 13 is provided on the X-beam stopper 12. In a non-limitative example, the conductive liner 13 may also be provided on the supporting board 11, so as to be located between the X-beam stopper 12 and the supporting board 11.

In certain applications as shown, for example, in FIG. 1, the conductive liner 13 is an integral structure, which is provided between the glass panel 14 and the supporting board 11. Embodiments may be selectively provided with a black ethylene film 15 to absorb part of the X-beam penetrating the glass panel 14, while other embodiments may not be provided with the black ethylene film 15, e.g., the conductive liner 13 may be arranged to be in black color such that not only the safety of the glass panel is ensured, but also the cost is saved.

Figure 3:
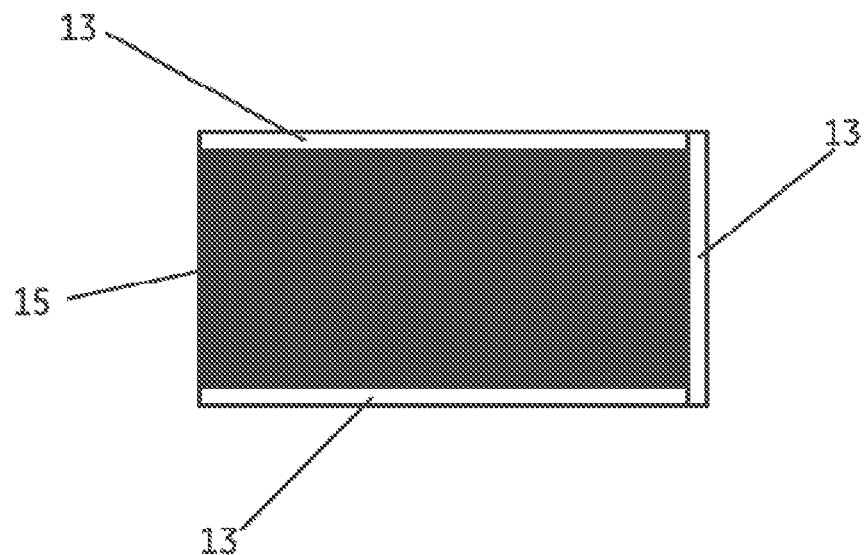
FIG. 3 and FIG. 4 are installation schematic diagrams of different embodiments of a conductive liner of the detector shown in FIGS. 1 and 2.
Figure 4:
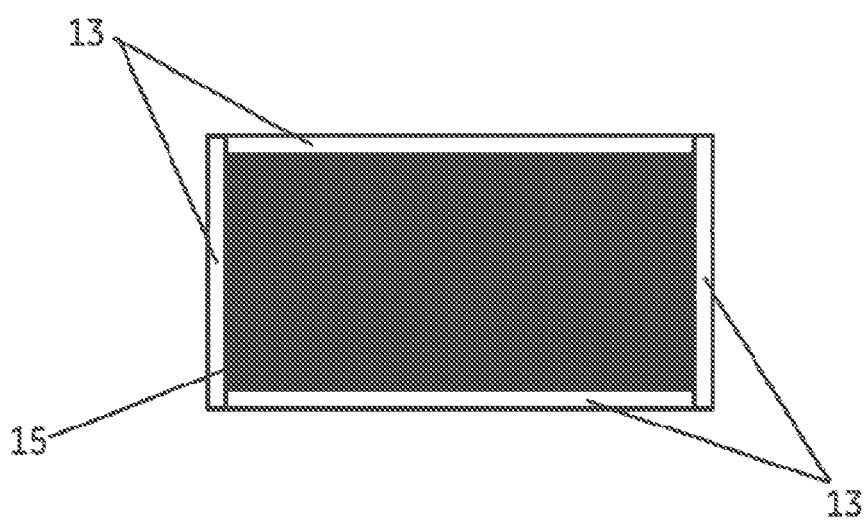

In other examples and embodiments, the conductive liner 13 may be arranged to be in stripe shape. In one example, as shown in FIG. 3, the black ethylene film is provided on the X-beam stopper 12 and the conductive liner 13 is provided on three sides of the ethylene film in the form of stripes such that the glass panel is provided on this structure. In another example, as shown in FIG. 4, according to different requirements, the conductive liner 13 may also be provided on four sides of the ethylene film in the form of stripes.

In at least one embodiment, the detector 10 is provided with the conductive liner 13 of a certain flexibility located between the glass panel 14 and the supporting board 11. In comparison with the conventional structure using an aluminum board, the structure disclosed herein may not need to still use the aluminum board, which decreases the processing difficulty and saves the cost. Meanwhile, since the conductive liner 13 is used, the black ethylene film may be omitted to further save the cost in a certain application. In addition, since the conductive liner 13, which is provided between the glass panel 14 and the supporting board 11, has a certain flexibility, it may buffer and eliminate the external vibration or shock such that the glass panel 14 may be better protected from being damaged. Furthermore, since the conductive liner 13 is used, the structure of the detector 10 is simplified and thus easy to be manufactured.

Although the invention presented herein has been described in conjunction with certain non-limiting examples and embodiments, those skilled in the art may understand that various modifications and variations could be made to the present invention. Therefore, it should be recognized that the claims are intended to cover all these modifications and variations within the true spirit and scope of the presented examples and embodiments.

What is claimed is:

1. A detector for medical diagnosis, comprising:
   a photosensitive element used for sensing an X-ray;
   an X-ray stopping element used for stopping the X-ray from penetrating said photosensitive element, wherein the X-ray stopping element comprises a first side and a second side opposite the first side;
   a supporting board provided below the X-ray stopping element to be used for supporting said photosensitive element, wherein the X-ray stopping element directly contacts the supporting board;
   a conductive liner provided between said photosensitive element and said supporting board to fit with said photosensitive element, wherein said photosensitive element directly contacts said conductive liner, wherein the X-ray stopping element directly contacts said supporting board on the first side and directly contacts said conductive liner on the second side; and
   a black ethylene film provided between said photosensitive element and said supporting board, wherein said conductive liner is provided on at least three sides of said black ethylene film in the form of stripes.

2. The detector for medical diagnosis according to claim 1, wherein said photosensitive element is a photosensitive glass panel.

3. The detector for medical diagnosis according to claim 1, wherein said conductive liner is provided between said photosensitive element and said X-ray stopping element.

4. The detector for medical diagnosis according to claim 1, wherein said conductive liner is provided between said photosensitive element and said X-ray stopping element in an integral structure.

5. The detector for medical diagnosis according to claim 1, wherein said conductive liner is a flexible liner.

6. The detector for medical diagnosis according to claim 1, wherein said conductive liner is provided on four sides of said ethylene film in the form of stripes.

7. A detector for medical diagnosis, comprising:
   a photosensitive element used for sensing an X-ray;
   an X-ray stopping element used for stopping the X-ray from penetrating said photosensitive element;
   a supporting board provided below the X-ray stopping element to be used for supporting said photosensitive element;
   a conductive liner provided between said photosensitive element and said supporting board to fit with said photosensitive element; and
   a black ethylene film provided between said photosensitive element and said supporting board, wherein said conductive liner is provided on at least three sides of said black ethylene film in the form of stripes.

* * * * *